United States Patent [19]
Piazzi et al.

[11] 3,990,852
[45] Nov. 9, 1976

[54] IMMUNOLOGICAL ANALYSIS APPARATUS
[75] Inventors: Sergio Piazzi; Alberto Bracciali; Sandra Sordi, all of Siena, Italy
[73] Assignee: Instituto Sieroterapico e Vaccinogeno Toscano "Sclavo" S.p.A., Siena, Italy
[22] Filed: Aug. 12, 1975
[21] Appl. No.: 604,065

[30] Foreign Application Priority Data
Aug. 20, 1974 Italy.................................. 9552/74

[52] U.S. Cl............................... 23/253 R; 195/139
[51] Int. Cl.².................... C12K 1/10; G01N 31/02; G01N 33/16
[58] Field of Search ............. 23/253 R, 230 B, 292; 204/180 G, 299 R; 195/139

[56] References Cited
UNITED STATES PATENTS
3,554,704   1/1971   Ushakoff.......................... 23/253 R
3,674,438   7/1972   Shen ................................ 23/253 R OTHER PUBLICATIONS
A. J. Croyle, Immunodiffusion, pp. 203–205, 215, 216, (1961).

Primary Examiner—Joseph Scovronek
Attorney, Agent, or Firm—Haseltine, Lake & Waters

[57] ABSTRACT

Apparatus for carrying out double or radial immunodiffusion analysis comprises a circular plate with an upstanding rim therearound. One face of the plate and the rim together form a trough within which a diffusion medium layer can be formed. A plurality of cylindrical walls project from the opposite face of the plate and define sample wells which open via respective apertures in the plate into the trough. Samples to be analysed are placed in the wells from where they diffuse into a said diffusion medium layer formed in the trough. External contamination is prevented by a cover which engages the rim to enclose the trough, and by a sealing film placed over the ends of the cylindrical walls remote from the plate to close off the wells.

9 Claims, 6 Drawing Figures

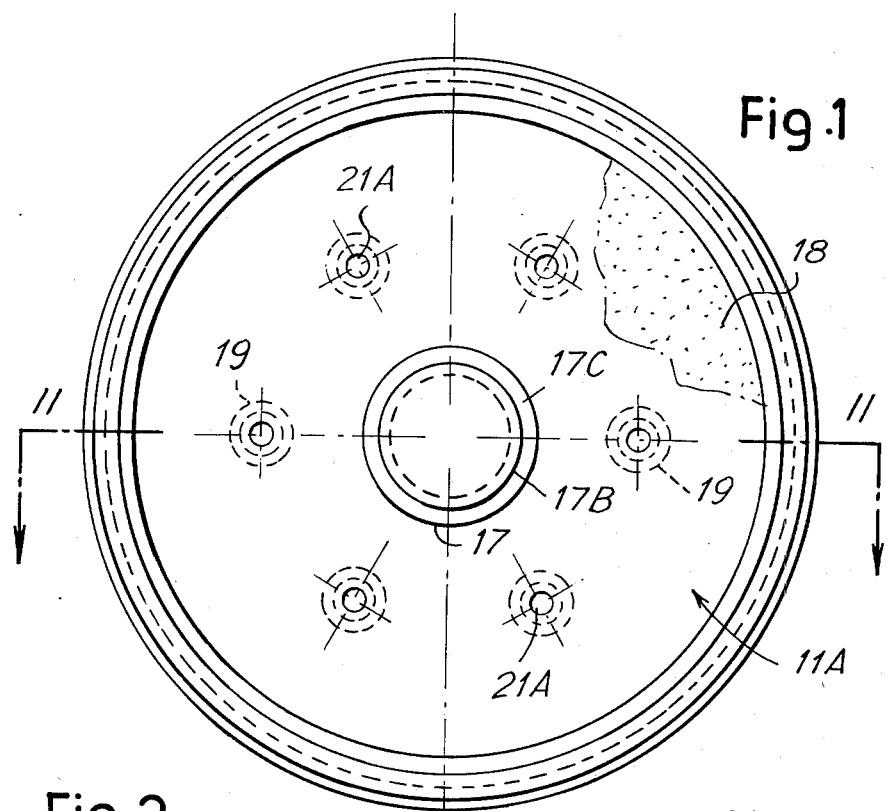
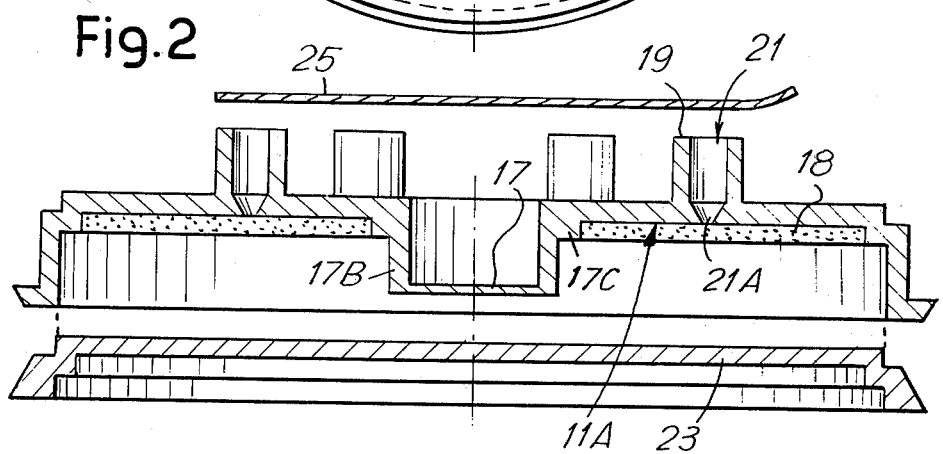
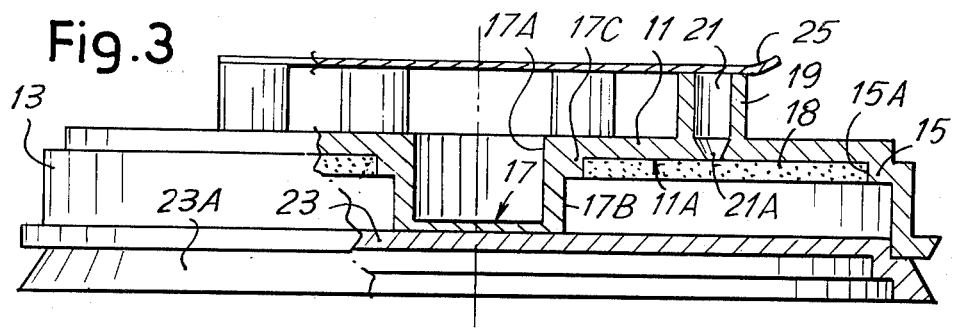

IMMUNOLOGICAL ANALYSIS APPARATUS

BACKGROUND OF THE INVENTION

1. Field of the Invention

This invention relates to apparatus for use in carrying out immunological analysis, such as immunological analysis by double and radial immunodiffusion methods in an agar gel layer or other diffusion medium.

2. Description of the Prior Art

Both radial and double immunodiffusion analysis methods depend on two dimensional diffusion through a diffusion medium.

In radial immunodiffusion analysis, a fluid which, for example, contains an antigen is introduced at a particular location into the diffusion medium (for example, an agar gel layer) in which a specific antiserum is incorporated. A precipitate halo is produced as the antigen diffuses into the agar gel and reacts with the antiserum, the final area of the halo being a measure of the concentration of the initial antigen fluid.

Double immunodiffusion analysis is used to compare the reactions of, for example, two different antigen solutions with the same antiserum solution, all three solutions being introduced at respective locations in an agar gel layer and being allowed to diffuse towards each other.

Both the radial and double immunodiffusion analysis methods have been previously carried out by forming the diffusion medium layer in a Petri dish and then introducing the test solutions into depressions of predetermined sizes and spacings made in the medium. To reduce external influences, a cover can be placed on top of the diffusion layer. This technique for radial and double immunodiffusion analysis has several disadvantages including the need to select for each analysis a particular depression size and spacing, the formation of a diffusion layer meniscus which, owing to more rapid drying in the region of the meniscus, tends to attract the diffusing solutions, and a generally poor sensitivity. Further, diffusion is usually slow owing to the almost total enclosure of the diffusion medium which inhibits evaporation therefrom.

It is an object of the invention to provide improved apparatus for carrying out radial and double immunodiffusion analysis.

SUMMARY OF THE INVENTION

According to the invention there is provided apparatus for carrying out double or radial immunodiffusion analysis, comprising plate means, a rim extending around the periphery of the plate means and defining therewith a trough wherein a diffusion medium layer can be formed, the plate means defining a plurality of sample wells with respective openings into said trough, said wells having a minimum cross-sectional area at their respective said openings, a cover engaging around the rim and extending across said trough whereby to cover a said diffusion medium formed therein, and film sealing means for closing off the said wells at their ends remote from their said openings.

According to the invention there is also provided apparatus for carrying out double or radial immunodiffusion analaysis, comprising a circular plate having first and second opposite faces and defining a plurality of apertures arranged symmetrically around said plate and extending therethrough, a plurality of wall means projecting from the said first face of the plate, each wall means surrounding a respective said aperture and defining a space in communication therewith, said space and aperture together forming a sample well, a rim extending around the periphery of the plate and projecting from said second face, said rim and said second face defining a trough wherein a diffusion medium layer can be formed, first sealing means closing off the said wells at their ends remote from the plate, and second sealing means engaging with the said rim to enclose said trough, the first and second sealing means together isolating a said diffusion medium layer formed in the trough from external contamination.

BRIEF DESCRIPTION OF THE DRAWINGS

Apparatus embodying the invention, and for use in immunological analysis, will now be particularly described, by way of example, with reference to the accompanying diagrammatic drawings, in which:

FIG. 1 is a plan view of apparatus for use in carrying out radial immunodiffusion analyses;

FIG. 2 is a section taken on line II—II of FIG. 1 and shows the apparatus with its cover removed;

FIG. 3 is a part-sectional view similar to that of FIG. 2 but showing the cover in position;

Figure 4:
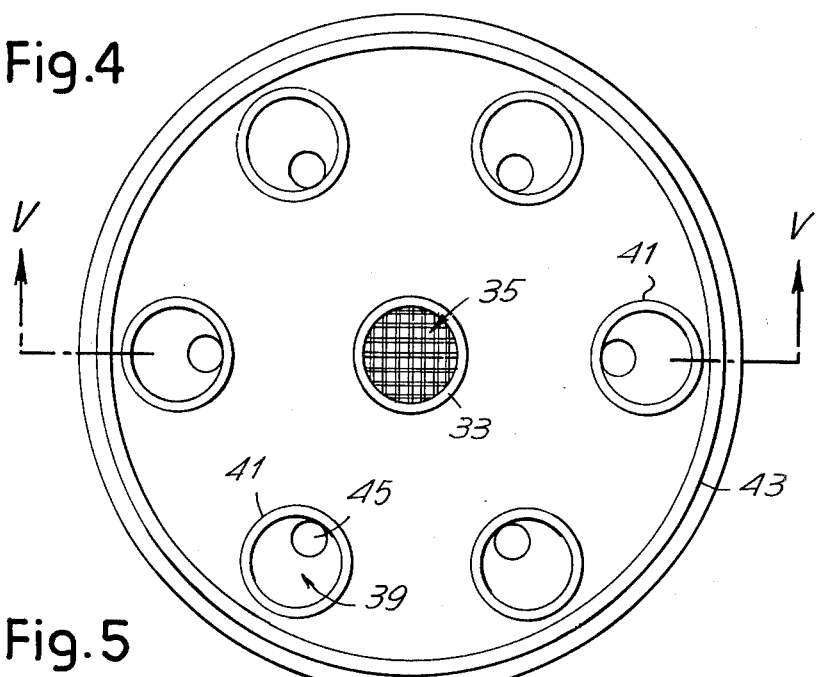
FIG. 4 is a plan view of apparatus for use in carrying out double immunodiffusion analyses.

As is shown in FIGS. 1 to 3, the radial immunodiffusion apparatus comprises a dish-shaped vessel formed by a circular plate 11 with an upstanding rim 13, and a protective cover 23 for the vessel. The plate 11 is made of a transparent material and joins the rim 13 at a step 15 of the rim, the inner cylindrical surface 15A of the step 15 bounding the adjoining surface 11A of the plate 11. The plate 11 has a central hollow hub 17, formed by a cylindrical wall 17B, which projects on the same side of the plate 11 as the rim 13. A step 17C extends around the base of the hub 17. A shallow annular trough is defined by the surface 15A, the opposite cylindrical surface of the step 17C, and the surface 11A. An agar gel layer 18 fills the annular trough.

A plurality of apertures 21A extend through the plate 11 and are each surrounded, on the opposite side of the plate 11 to the surface 11A, by a cylindrical wall 19 which projects away from the plate 11. The space enclosed by each wall 19 together with the corresponding aperture forms a sample well 21 for receiving samples to be analysed. The apertures 21A taper slightly towards the plate surface 11A. In oder to minimise the influences on an analysis of edge effects which occur at the radially inner and outer boundaries of the agar gel layer 18, the apertures 21A are positioned approximately midway between the surface 15A and the opposite surface of the step 17C.

The heights of the steps 15 and 17C are both equal to the thickness of the agar gel layer 18. These steps are provided to enable the layer 18 to be formed without a meniscus at its edges, the steps 15 and 17C respectively defining the radially outer and inner boundaries of the layer 18.

The cover 23 has a rim 23A and fits over the end of the rim 13. An adhesive film 25 is provided to cover the upper edges of the walls 19 and thereby seal off the wells 21.

In FIGS. 2 and 3 the apparatus is illustrated prepared for use, that is, the agar gel layer 18 has been formed in the shallow annular trough defined by the surface 11A and steps 15 and 17C. To form the layer 18, the apparatus, which advantageously already has a film 25 covering the wells 21, is placed the opposite way up to that shown in FIGS. 2 and 3 and the shallow trough is filled with an agar gel layer 18. The cover 23 is the applied and the apparatus can be stored in this state with the film 25 and the cover 23 in place until required.

When it is desired to carry out a radial immunodiffusion analysis, the apparatus is orientated as illustrated in FIG. 3 and the adhesive film 25 is removed. Next, the wells 21 are filled with samples of the substances to be analysed and the film 25 is then re-applied. Introduction of the substances into the wells 21 can be easily done using syringes or similar injection devices.

Instead of using the film 25 to close off the wells 21 after introduction of the substances to be analysed, the cover 23 can be placed on top of the walls 19 to seal off the wells 21, the space bounded by the rim 13 and the surface 11A being in this case closed off by placing the apparatus with the rim 13 projecting downwardly onto a working surface (for example, a slab of glass or marble). Alternatively other means can be used to cover the wells 21.

Analytical measurements of the effects of diffusion of the substances under analysis through the agar gel layer are readily effected owing to the transparent nature of the plate 11 and also because a caliper or other measuring gauge can be brought right up to each well 21.

Figure 5:
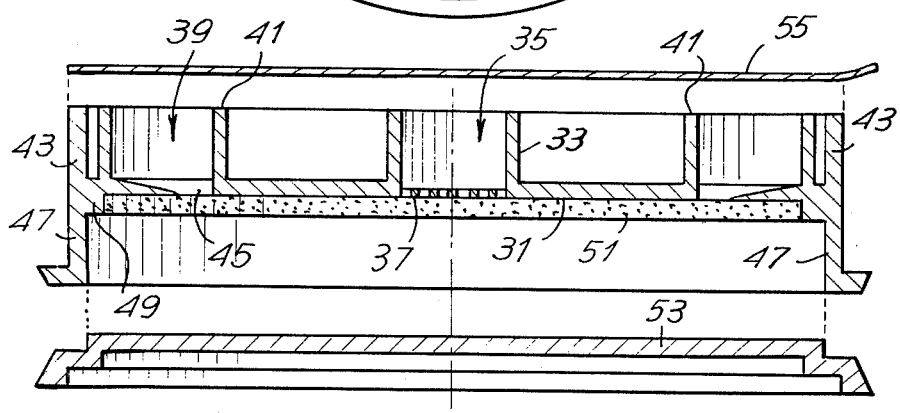
FIG. 5 is a section taken on line V—V of FIG. 4 and shows the apparatus with its cover removed.
Figure 6:
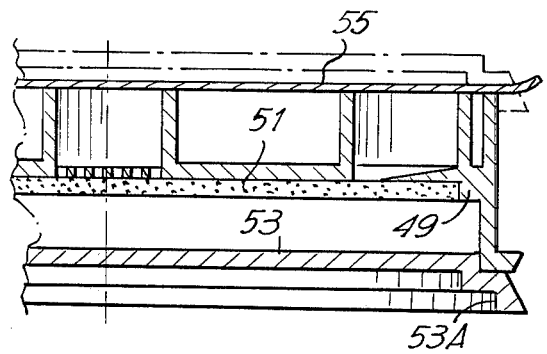
FIG. 6 is a fragmentary section similar to that of FIG. 5 but showing the cover in position.

The double immunodiffusion apparatus shown in FIGS. 4 to 6 comprises a circular plate 31 from one side of which projects a central hollow hub formed by a cylindrical or prismatic wall 33. The wall 33 defines a well 35 which is provided with a wide sieve-like bottom 37 in the plane of the plate 31. The plate 31 has a cylindrical rim formed by rim portions 43 and 47 which respectively project on the same and on the opposite side of the plate 31 as the wall 33. A plurality of apertures are formed in the plate 31, and each aperture is surrounded on the same side of the plate 31 as the wall 33 by a respective cylindrical wall 41 positioned adjacent the rim portion 43. The space enclosed by each wall 41 together with the corresponding aperture form a sample well 39.

The opening 45 of each aperture in the surface of the plate opposite to that from which the walls 41 project, is offset with respect to the axis of the corresponding cylindrical wall 41 in a direction towards the centre of the plate 31.

The rim portion 47 joins the plate 31 at a circumferential step 49 of the rim portion 47. The inner cylindrical surface of the plate 31 opposite to the one from which the walls 33 project together define a shallow circlar trough which is filled by an agar gel layer 51. The gel layer 51 does not extend into the well 35 owing to the presence of the sieve-like bottom 37, or into the wells 39 owing to the limited sizes of the openings 45. The layer 51 is meniscus-free as its thickness equals the height of the step 49.

A cover 53 can be placed over the rim portion 47 to close the space within which the layer 51 is located in order to preserve the layer (FIG. 6). A self-adhesive film 55 is applied across the tops of the rim portion 43 and of the walls 41 and 33.

The cover 53 can be kept in the position shown in FIG. 6 during and after introduction of samples to be analysed into the wells 35 and 39 (this introduction being effected by removal of the film 55). Alternatively, the cover 55 can be used to close off the wells 35 and 39 by engagement of a step-like edge 53A of the cover 53 around the outside of the rim portion 43.

Advantageously, each aperture is inclined like a hopper from the base of its corresponding wall 41 towards its opening 45. The offsetting of the openings 45 of each well 39 towards the centre of the plate 31 enables the plate diameter to be reduced for a given spacing between the openings 45 and the centre well 35 and between the openings 45 and the step 49 defining the periphery of the agar gel layer.

For both the described apparatuses where the wells 21 (or 39) are only required to have a small volume, the wells can be formed entirely in the thickness of the plate 11 (or 31), thus dispensing with the walls 19 (or 41).

As already described, both the illustrated apparatuses enable a meniscus-free agar gel layer to be formed. This is of advantage in carrying out accurate analyses since a meniscus in the agar gel layer would attract the diffusing substances as a result of the more rapid drying which occurs at the meniscus as compared with elsewhere in the layer.

In normal laboratory use of the apparatus, the apparatus would be supplied from a store with the layer 18 (or 51) already formed, the cover 23 (or 53) in place, and the wells 21 (or 35 and 39) empty and closed by the film 25 (or 55). Thus all the user has to do to carry out an analysis, is to introduce the solutions to be analysed into the wells using, for example, a microsyringe. The quantity of solution introduced can be, for example, up to 120 micro-litres. A wet chamber is not required, because the diffusion is effected under ambient conditions.

Another advantage of the apparatuses herein described is that unlike previously-proposed arrangements in which the agar gel layer is almost completely enclosed, the described apparatuses allow evaporation to occur from the agar gel layer, which results in reduced diffusion times.

The apparatus described herein also enable the volumes of the samples under analysis to be varied while the diameters of the openings of the wells onto the agar layer remain fixed. Further, in the double immunodiffusion device the distance between the central well 35 (which for example holds an antigen solution) and the wells 39 (containing antiserum) is constant; the volumes of both the antigen and antiserum per well being, for example, varied up to 120 micro-litres. The constancy of the well parameters greatly speeds analysis in comparison with previously proposed arrangements in which the diameters and spacings of the antigen and antiserum depressions in the agar gel layer had to be selected for each analysis.

Typical applications of the apparatuses described herein include the analysis of antigens having a bacterial origin and of the associated antibodies; the analysis of human plasmatic fractions and of biological liquids in the normal and the pathologic state; the analysis of antigens of vegetable origin; and the analysis of hormones.

Although the double and radial immunodiffusion analysis methods have previously been considered to be of low sensitivity as compared with other available methods (for example, radioimmunoassay, and the fixing of the complement method), they continue to play an important role in immunology. However, the increased sensitivity obtainable by use of the apparatuses herein described should permit wider usage of the double and radial immunodiffusion techniques.

We claim:

1. Apparatus for carrying out double or radial immunodiffusion analysis, comprising
    plate means,
        a rim extending around the periphery of the plate means and defining therewith a trough wherein a diffusion medium layer can be formed, the plate means defining a plurality of sample wells with respective openings into said trough, said wells having their minimum cross-sectional area at their respective said openings,
        a cover engaging around the rim and extending across said trough whereby to cover a said diffusion medium layer formed therein, and
        film sealing means for closing off the said wells at their ends remote from their said openings.

2. Apparatus according to claim 1, in which each said well comprises a cylindrical first portion, and a second portion which tapers from said first portion to the said opening of the well.

3. Apparatus according to claim 1, in which the rim is provided with a step adjoining the said plate means, the inward-facing surface of the step defining the outward extent of said trough.

4. Apparatus according to claim 1, in which the plate means comprises
    a plate having first and second opposite faces, the plate defining a plurality of apertures which extend between said first and second faces and which form said well openings in the first face of the plate, and
    a plurality of wall means projecting from the said second face of the plate, each wall means surrounding a respective said aperture to define a space in communication therewith, said space and aperture forming a said sample well, the film sealing means being applied across the ends of the wall means remote from the plate.

5. Apparatus according to claim 4, in which the rim projects away from the plate on the sides of both the first and second faces, the rim extending out on the side of the said second face as far as the said wall means.

6. Apparatus according to claim 1 and for carrying out radial immunodiffusion analysis, comprising a central step formed centrally on the said plate means and having an outwardly directed surface which forms a boundary of the said trough, the said well openings being equi-spaced from the said step and the rim.

7. Apparatus according to claim 1 and for carrying out double immunodiffusion analysis, wherein the said well openings are offset towards the centre of the plate means with respect to the wells.

8. Apparatus according to claim 7, wherein one said well defined by the plate means is positioned centrally thereof and has a said opening of greater cross-sectional area than the openings of the other said wells, the opening of the central well having sieve means thereacross.

9. Apparatus for carrying out double or radial immunodiffusion analysis, comprising a circular plate having first and second opposite faces and defining a plurality of apertures arranged symmetrically around said plate and extending therethrough, a plurality wall means projecting from said first face of the plate, each wall means surrounding respective said aperture and defining a space in communication therewith, said space and aperture together forming a sample well, said well having its minimum cross-sectional area at its respective opening, a rim extending around the periphery of the plate and projecting from said second face, said rim and said second face defining a trough wherein a diffusion medium layer can be formed, first sealing means closing off said wells at their ends remote from the plate, and second sealing means engaging with said rim to enclose said trough, the first and second sealing means together isolating said diffusion medium layer formed in the trough from external contamination.

* * * * *